(12) United States Patent
Roizen

(10) Patent No.: US 7,976,879 B2
(45) Date of Patent: Jul. 12, 2011

(54) NUTRITIONAL SUPPLEMENT PRODUCT TO SUPPRESS AGE-RELATED DECLINE IN COGNITIVE CAPACITY AND OTHER AGING FUNCTIONS

(76) Inventor: Michael F. Roizen, Shaker Heights, OH (US)

(*) Notice: Subject to any disclaimer, the term of this patent is extended or adjusted under 35 U.S.C. 154(b) by 4 days.

(21) Appl. No.: 12/508,277

(22) Filed: Jul. 23, 2009

(65) Prior Publication Data

US 2009/0285938 A1    Nov. 19, 2009

Related U.S. Application Data

(63) Continuation-in-part of application No. 11/592,050, filed on Nov. 2, 2006, now abandoned.

(60) Provisional application No. 60/733,394, filed on Nov. 4, 2005.

(51) Int. Cl.
| | |
|---|---|
| A61K 36/00 | (2006.01) |
| A61K 31/455 | (2006.01) |
| A61K 36/82 | (2006.01) |
| A61K 38/43 | (2006.01) |
| A61K 36/20 | (2006.01) |
| A61K 9/48 | (2006.01) |
| A61K 33/42 | (2006.01) |
| A61K 33/06 | (2006.01) |
| A61K 8/26 | (2006.01) |
| A23L 1/30 | (2006.01) |
| A23L 1/36 | (2006.01) |
| A23C 21/00 | (2006.01) |
| A23G 1/00 | (2006.01) |
| A23B 7/157 | (2006.01) |

(52) U.S. Cl. ............ 424/725; 426/73; 426/72; 426/583; 426/584; 426/593; 426/632; 426/267; 424/771; 424/451; 424/602; 424/682; 424/702; 424/67; 424/94.1; 424/729; 514/725; 514/474

(58) Field of Classification Search .................. None
See application file for complete search history.

(56) References Cited

U.S. PATENT DOCUMENTS

| | | | |
|---|---|---|---|
| 4,888,187 A | 12/1989 | Given et al. | |
| 5,480,865 A | 1/1996 | Kingham | |
| 5,697,203 A * | 12/1997 | Niwa | ........... 53/510 |
| 6,171,635 B1 * | 1/2001 | Zhao | ........... 426/596 |
| 6,352,713 B1 | 3/2002 | Kirschner et al. | |
| 6,391,310 B1 | 5/2002 | Empie et al. | |
| 6,572,899 B1 * | 6/2003 | Gorsek | ........... 424/732 |
| 6,642,259 B1 | 11/2003 | Meydani et al. | |
| 7,030,092 B1 | 4/2006 | Levine | |
| 2002/0018807 A1 | 2/2002 | Schmitz et al. | |
| 2002/0173549 A1 * | 11/2002 | Wurtman et al. | ........... 514/625 |
| 2003/0108594 A1 | 6/2003 | Manning et al. | |
| 2003/0147995 A1 | 8/2003 | Koss et al. | |
| 2004/0258734 A1 | 12/2004 | Nawar | |
| 2005/0002992 A1 | 1/2005 | McCleary et al. | |
| 2005/0101660 A1 | 5/2005 | Lee | |
| 2005/0186306 A1 | 8/2005 | Sonneveld et al. | |
| 2007/0031486 A1 | 2/2007 | Squashic et al. | |
| 2007/0087084 A1 | 4/2007 | Coleman et al. | |

FOREIGN PATENT DOCUMENTS

| | | |
|---|---|---|
| CA | 2401452 A1 * | 3/2003 |
| EP | 1 302 111 A1 | 4/2003 |
| EP | 1 774 856 A1 | 4/2007 |
| NZ | 530554 A * | 4/2004 |
| WO | WO 01/64044 A2 | 9/2001 |
| WO | WO 02/094035 A1 | 11/2002 |
| WO | WO 2004/103090 A2 | 12/2004 |

OTHER PUBLICATIONS

Smit et al, Methylxanthines are the psycho-pharmacologically active constituents of chocolate, Psychopharmacology, 2004, 176 (3-4): 412-9.*
Plech et al, Effect of L-arginine on memory in rats, Polish Journal of Pharmacology, 2003, 55 (6): 987-92.*
Rampersaud et al, Breakfast habits, nutritional status, body weight, and academic performance in children and adolescents, Journal of the American dietetic association, 105 (5): 743-760, May 2005.*
Sumien et al, Effect of long-term coenzyme Q10 supplementation on psychomotor and cognitive functions in young and adult mice, Society for neuroscience Abstract Viewer and Itinerary Planner, (2003). vol. 2003, pp. Abstract No. 98.9.*
Seidl et al, A taurine and caffeine-containing drink stimulates cognitive performance and well-being, Amino acids, 2000, 19: 635-642.*
Extended European Search Report, European Application 06836991.7. European Patent Office, Feb. 26, 2010 (16 pages).
International Preliminary Report on Patentability, PCT/US2006/043229; Mar. 24, 2009, 6pgs.
International Search Report & Written Opinion of International Searching Authority, PCT/US2006/043229; Oct. 3, 2008, 8pgs.

* cited by examiner

*Primary Examiner* — Qiuwen Mi
(74) *Attorney, Agent, or Firm* — The Marbury Law Group PLLC

(57) ABSTRACT

A product and method for administering daily micronutrient requirements (DMRs) comprising vitamins, minerals and essential fatty acids targeted to reduce appetite and/or the risks associated with aging and associated cognitive impairment. The DMRs are administered to individuals via food products. In an embodiment of the present invention, the DMRs are offered in the form of a health bar, smoothie, or drink. The DMRs may be incorporated into other forms without departing from the scope of the present invention. By way of illustration and not as a limitation, the constituents may be incorporated into a fruit or yogurt "smoothie," a frozen desert such as an ice cream or sorbet, and a beverage.

10 Claims, No Drawings

NUTRITIONAL SUPPLEMENT PRODUCT TO SUPPRESS AGE-RELATED DECLINE IN COGNITIVE CAPACITY AND OTHER AGING FUNCTIONS

CROSS REFERENCE TO RELATED APPLICATION

This application is a continuation in part of U.S. application Ser. No. 11/592,050 filed Nov. 2, 2006 now abandoned which claims priority benefit under 35 U.S.C. §119(e) from provisional application No. 60/733,394, filed Nov. 4, 2005, both of which applications are incorporated by reference herein in their entirety for all purposes

FIELD OF THE INVENTION

This application relates generally to nutritional supplements delivered in various forms.

BACKGROUND INFORMATION

Aging affects all parts of the human system. Bones can become thinner and less dense, joints may fail because of loss of cartilage, the circulatory system may become clogged, the heart may lose muscle or strength of contraction (or even fail), and mental/cognitive processing speed or capacity may decline.

It has been shown that a healthy diet, regular physical activity program and positive attitude can help delay the onset and slow the progression of many age-related changes. What constitutes a "healthy" diet is an often debated topic and the subject of books and talk-shows. What is generally accepted is that it is not always easy for individuals to maintain a healthy diet or to acquire the nutrients that are beneficial for good health and for various abatement of the effect of various ailments and aging processes.

To many individuals, convenience foods are an attractive alternative to purchasing fresh foods and preparing meals. However, convenience foods are often high in calories and low in nutrients and fiber. Nutritional supplements in pill or tablet form may be helpful but must be taken regularly and provide little if any culinary gratification.

Various embodiment disclosed herein comprise nutritional supplement comprising specific portions of daily micronutrient requirements (e.g., vitamins, minerals, essentially fatty acids) targeted to reduce the risks associated with aging, that is consumable in a form that is both tasty and palatable, as for example, before a meal. Such a nutritional supplement may also provide appetite suppressant effects.

One embodiment provides a method for administering daily micronutrient requirements (DMRs) made up of vitamins, minerals and essential fatty acids targeted to reduce risks associated with aging, and/or decrease the speed of aging. The DMRs are administered to individuals via food products. According to one embodiment, the DMRs are offered in the form of a health bar. In general, the DMRs may be embodied as comestibles having other form factors without departing from the scope of the invention. By way of illustration and not as a limitation, the constituents may be incorporated into a "smoothie" (fruit, vegetable, nut oil, or yogurt based), a frozen desert (e.g., ice cream or sorbet), and a beverage. For purposes of this application, these various forms will be referred to as "nutritional supplement products."

In an exemplary embodiment, the DMRs are combined with other ingredients to form a nutritional supplement (nutritional supplement) that is consumed before a meal. Used in this way, the nutritional supplement also serves to suppress appetite by both specific means (releasing cholycystokinin and/or stimulating vagal afferents or as yet undetermined mechanisms). The DMRs embodied as a nutritional supplement may be varied in composition to suit the needs of particular men and women of various groups, for example but not as a limitation, statin users, non-statin users, those suffering from mild to severe cognitive impairment.

Thus, one mode of practice of the invention is to provide an appetizer nutritional supplement (nutritional supplement) containing daily micronutrient requirements that include vitamins, minerals and essentially fatty acids targeted to reduce the risks associated with aging, and which is consumable in a form that is pleasing in flavor, texture, and consistency, as for example, before a meal.

Another embodiment provides an appetizer nutritional supplement that suppresses appetite.

Another embodiment provides an appetizer nutritional supplement that suppresses appetite via release of cholycystokinin and/or stimulating vagal or other nervous afferents or efferents.

Another embodiment tailors the content of an appetizer nutritional supplement to the needs of particular groups of persons.

Another embodiment tailors the content of an appetizer nutritional supplement to the needs of particular groups of persons suffering from mild to severe cognitive impairment.

Another embodiment provides an appetizer nutritional supplement in the form of a health bar.

Another embodiment provides an appetizer nutritional supplement in the form of a frozen desert.

Another embodiment provides an appetizer nutritional supplement in the form of a beverage.

It is even another mode of practice of the invention to provide an appetizer nutritional supplement in the form of a "smoothie" type product.

A supplement according to at least some embodiments may be directed to reducing the risk of age related diseases such as cancer and arterial aging diseases including heart disease, sudden death from arrhythmias, stroke, cognitive impairment, memory loss, Alzheimer's Disease (AD), impotence and even wrinkled skin, and/or age related decline in functional capacity in cardiovascular or nervous or immune or musculosketal systems.

These modes of practice, as well as the various embodiments discussed will become apparent from a review of the detailed and general descriptions of the present application.

DETAILED DESCRIPTION

An embodiment of the present invention provides a method for administering daily micronutrient requirements (DMRs) composed of vitamins, minerals and essential fatty acids targeted to reduce the risks associated with various conditions of aging. The DMRs are administered to individuals via food products. In one embodiment, the DMRs are offered in the form of a health bar. The DMRs may be incorporated into other forms without departing from the scope of the invention. By way of illustration and not as a limitation, the DMRs may be incorporated into a fruit or yogurt "smoothie," a frozen desert such as an ice cream or sorbet, and a beverage. All of these forms are referred to collectively herein as "nutritional supplements."

According to another embodiment, the DMRs are combined with other ingredients to form an appetizer nutritional supplement (nutritional supplement) that is consumed before a meal. In this way, the nutritional supplement also serves to suppress appetite, by direct action or indirectly such as releasing cholycystokinin or stimulating the afferent vagas nerve by nutritional means or by other nervous or endocrine mechanisms. Further, various embodiments target genes responsible for various levels of cognitive impairment and AD.

Example 1

The DMRs to be put in a nutritional supplement may be varied to suit the needs of particular groups. In a first example embodiment, a nutritional supplement for a statin user in the form of a health bar comprises ½ ounce walnuts, three ground dark chocolate nubbins, ground no-calorie caramel, fillers that are high in fiber. The DMRs to be included in the example embodiment's health bar are vitamins as listed in Table 1, below. It is noted that folate is commonly referred to as "vitamin F" (alternately termed a B vitamin by some authorities) and is the anion form of folic acid.

TABLE 1

Vitamins for 1st example embodiment.

| VITAMIN | APPROX. AMOUNT |
|---|---|
| A | up to 2500 IU |
| $B_6$ | 2 mg |
| $B_{12}$ | 400 mcg |
| C | 50 mg |
| D | up to 1000 IU |
| E | 50 IU |
| F (folate) | 400 mcg |
| Thiamin | 12.5 mg |
| Riboflavin | 12.5 mg |
| Niacin | 15 mg |
| Biotin | 150 mg |
| Pantothenic acid | 150 mg |

The DMRs for the first example embodiment's health bar also include minerals as listed in Table 2, below.

TABLE 2

Minerals for 1st example embodiment.

| MINERALS | APPROX. AMOUNT |
|---|---|
| Calcium | up to 1600 mg |
| Magnesium | up to 400 mg |
| Selenium | 100 mcg |
| Zinc | 7.5 mg |
| Potassium | 0 mg |

The DMRs for the first example embodiment's health bar also include vitamin-like substances as listed in Table 3, below.

TABLE 3

Vitamin-like substances for 1st example embodiment.

| VITAMIN-LIKE SUBSTANCES | APPROX. AMOUNT |
|---|---|
| Lycopene | 30 mg |
| Lutein | 20 mg |
| Alpha lipoic acid | up to 200 mg |
| Acetyl-L-carnitine | up to 1500 mg a day |

Example 2

According to a second example embodiment of the invention, an nutritional supplement for statin users further includes up to 1200 mg of Coenzyme Q10 as an ingredient, in addition to those listed above for the first example embodiment.

Example 3

According to a third example embodiment of the invention, the nutritional supplement includes the ingredients described in the first example, with each of the identified DMRs being in the range of 25-100% of the minimum daily requirements as established by the government (e.g., the U.S. Food and Drug Administration) for each such DMR.

Example 4

According to a fourth example embodiment of the invention, the nutritional supplement includes the ingredients described in the first example, with an alternative formulation being substituted for the ½ ounce of walnuts. Specifically, up to a gram of three fatty acids (alone or in combination) are substituted for actual walnuts. These three fatty acids are docosahexaenoic acid (DHA), eicosapentaenoic acid (EPA), and alpha-linolenic acid (ALA). ALA is found in walnuts, and DHA and EPA are related to ALA and have demonstrated cardiac health benefits.

Example 5

According to a fifth example embodiment of the invention, the nutritional supplement includes the ingredients described in the first example, except substituting blueberry extract for the carmel.

Example 6

According to a sixth example embodiment of the invention, the nutritional supplement includes the ingredients described in the first example, except substituting raspberry extract for the caramel.

Example 7

According to a seventh example embodiment of the invention, the nutritional supplement includes the ingredients described in the first example, with each of the identified DMRs being substantially the same, with the exception of vitamins C and E. For the seventh example, the quantities of vitamins C and E are boosted, as listed in Table 4, below.

TABLE 4

Vitamin quantities for 7th example embodiment.

| VITAMIN | APPROX. AMOUNT |
|---|---|
| C | 500 mg |
| E | 500 IU |

Example 8

According to an eighth example embodiment of the invention, the nutritional supplement includes the ingredients described in the first example, with each of the identified DMRs being substantially the same and further including additional DMRs identified in the listing in Table 5, below.

TABLE 5

Vitamin-like substances for 8th example embodiment.

| VITAMIN-LIKE SUBSTANCES | APPROX. AMOUNT |
|---|---|
| l-arginine | up to 70 mg |
| tyrosine | up to 180 mg |
| taurine | up to 70 mg |
| green tea catechins | up to 120 mg |
| caffeine | up to 20 mg |
| querecin | up to 10 mg |

The green tea catechins as a class may be used as an ingredient in the nutritional supplement, as listed in this example. Of the green tea catechins, epigallocatechin gallate (EGCG) is currently identified as a particularly useful antioxidant.

It has been demonstrated that consuming walnuts prior to a meal, at the levels indicated for some above examples, inhibits stomach emptying and suppresses appetite, and this and other substances consumed can stimulate release of cholycystokinin and or vagal or other nerve impulses that inhibit stomach emptying and or hunger.

One embodiment provides a method of reducing appetite when an nutritional supplement, including as ingredients walnuts, ground dark chocolate nubbins, ground no-calorie carmel, fillers that are high in fiber, and DMRs, is eaten 8 to 30 minutes before a meal. The appetite suppression affect, particularly of the walnut content of the nutritional supplement, is effective to reduce the amount of food consumed during the meal. It is understood that the mechanism of action that brings about the reduction in appetite is induced release of endogenous hormones or gut polypeptides or other substances that reduce appetite.

Sustained use of the nutritional supplement according to the method of reducing appetite is effective to support weight loss and reduction of waist size.

Studies have indicated that the combination of vitamins and minerals and micronutrients decreases sudden death and delays arterial aging. Studies further indicate that the combination of vitamins and minerals and micronutrients additionally provides some degree of protection against certain cancers.

Accordingly, another facet of the various embodiments is their use to reduce the risks and/or processes associated with aging, through administration of nutritional supplement products in the form of an appetizer bar (or other delivery mechanism) containing daily micronutrient requirements that include targeted vitamins, minerals and essentially fatty acids. To reduce the risks associated with aging, an nutritional supplement according to the various embodiments supports heart function, cognitive functions, supports arterial health, supports health of a subject's immune system, and supports reduction of defects in mitochondrial function.

The delivery mechanism is selected from among various diverse choices such that at least one mechanism will be pleasing in flavor, texture, and consistency to most any subject. Smoothies, frozen desserts, or beverages are all strategically available as delivery mechanisms for nutritional supplements delivered according to embodiments of the present invention.

Another embodiment provides a method for packaging a dietary supplement targeted to reducing the risks and or processes associated with aging. In this embodiment, a nutritional supplement comprises walnuts, ground dark chocolate nubbins, ground no-calorie caramel, fillers that are high in fiber, and DMRs in the form of a health bar. The health bar is packed in an airtight container. By way of illustration, and not as a limitation, the health bar is packed in an aluminized polyester film in the presence of nitrogen gas and dated for shelf life. Dry nitrogen gas (i.e., without water vapor) is particularly effective for practicing this embodiment. Although nitrogen is named as an example, other gasses that are relatively non-reactive are suitable. As a further illustration, and not as a limitation, the health bar is packed in the airtight container with a preserving substance added to the bar to preserve fats in the bar.

There are a number of ingredients in the nutritional supplement product for suppressing appetite, as disclosed in various embodiments. These ingredients interact with one another to suppress appetite but also provide other surprising benefits as they relate to cognitive function and prevention of cognitive impairment.

It is well known that regional cerebral glucose metabolic rates (rCMRgluc) are decreased in those with dementia and Alzheimer's Disease (AD). A decrease in rCMRgluc has also been found to a lesser extent in certain test subjects, as compared to control subjects, indicating an increased potential for dementia even though no symptoms are currently manifested. This decrease in cellular activity is also mirrored in the genes responsible for AD.

ApoE4 gene has been implicated in atherosclerosis, AD, and impaired cognitive function. ApoE is a nuclear receptor member that plays role in metabolism regulation of cholesterol, fatty acid and glucose homeostasis.

The E4 variant is the only unequivocal genetic risk factor for late-onset Alzheimer's disease in a variety of ethnic groups. Caucasian and Japanese carriers of 2 E4 alleles have between 10 and 30 times the risk of developing AD by 75 years of age, as compared to those not carrying any E4 alleles. The exact mechanism of how E4 causes such dramatic effects has not yet been fully determined. However, it is known that the isoform ApoE-$\epsilon$4 is not very effective in metabolizing glucose, resulting in increased vulnerability to Alzheimer's in individuals with that gene variant. The heterozygous pair of ApoE and E4 is less active than the homozygous for these genes. A mouse animal model can replicate the activity of the ApoE gene. The activity can also be measured in gene arrays from cells from affected and non-affected individuals.

A series of observations/experiments designed to compare the metabolic activities of individuals who consumed the nutritional supplement product, as disclosed in the various embodiments against a commercially available nutritional supplement bar manufactured by Nature Valley®, specifically the "Oats & Honey" Crunchy Granola Bar.

Experimental results associated with test subjects consuming the nutritional supplement product as described in the various embodiments, surprisingly showed an increase in the uptake of radioactive glucose in the ApoE4 gene or its normal variant. This increased glucose uptake indicates increased activity in the ApoE gene pair of these test subjects. This would therefore indicate a potential lessening of the risk of AD in those with the E4 variant of Apo.

In contrast, no increase in uptake of radioactive glucose was found in the ApoE4 gene or its normal variant in those test subjects consuming the Granola Bar.

We are not certain why this increase activity in the ApoE4 or ApoE gene occurs when consuming the nutritional supplement product with the ingredients as claimed versus the commercially available granola bar. Further, there did not appear to be a similar uptake in radioactive glucose as a result of consuming the ingredients noted in the various embodiments separately. Thus there appears to be a synergistic effect that results in a surprising additional benefit associated with consuming the nutritional supplement product having the ingredients as disclosed.

There is also a decrease in inflammatory markers that is found to be greater in individuals consuming the various embodiments nutritional supplement product as opposed to those consuming the ingredients noted separately.

A nutritional supplement product to suppress age-related disease, cognitive impairment and appetite has been shown. It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. A nutritional supplement product for inhibiting the progression of cognitive impairment in a statin user, the nutritional supplement comprising:
    about one half ounce of ground walnuts;
    three ground nubbins of dark chocolate;
    ground no-calorie caramel;
    high fiber filler;
    up to about 2500 IU of vitamin A;
    about 2 mg of vitamin B6;
    about 400 mcg of vitamin B12;
    about 50 mg of vitamin C;
    up to about 1000 IU of vitamin D;
    about 50 IU of vitamin E;
    about 400 mcg of folate;
    about 12.5 mg of Thiamin;
    about 12.5 mg of Riboflavin;
    about 15 mg of Niacin;
    about 150 mg of Biotin;
    about 150 mg of Pantothenic acid;
    up to about 1600 mg of Calcium;
    up to about 400 mg of Magnesium;
    about 100 mcg of Selenium;
    about 7.5 mg of Zinc;
    about 30 mg of Lycopene;
    about 20 mg of Lutein;
    up to about 200 mg of Alpha lipoic acid;
    up to about 1500 mg of Acetyl-L-carnitine;
    up to about 400 mg of Coenzyme Q10;
    up to about 70 mg l-arginine;
    up to about 180 mg tyrosine;
    up to about 70 mg taurine;
    up to about 120 mg green tea catechin;
    up to about 20 mg caffeine; and
    up to about 10 mg quercetin.

2. The nutritional supplement product for inhibiting the progression of cognitive impairment in a statin user according to claim 1, further comprising a preserving substance comprising a substantially non-reactive fluid.

3. The nutritional supplement product for inhibiting the progression of cognitive impairment in a statin user according to claim 2, wherein the substantially non-reactive fluid comprises nitrogen gas.

4. The nutritional supplement product for inhibiting the progression of cognitive impairment in a statin user according to claim 1 where the nutritional supplement product is of the form taken from the group consisting of a bar, a smoothie, a frozen desert, and a beverage.

5. The nutritional supplement product for inhibiting the progression of cognitive impairment in a statin user according to claim 1, wherein consumption of the nutritional supplement product supports function of statins in reducing inflammation.

6. The nutritional supplement product for inhibiting the progression of cognitive impairment in a statin user according to claim 5, wherein consumption of the nutritional supplement further supports appetite suppression.

7. A nutritional supplement product for inhibiting the progression of cognitive impairment in a non-statin user, the nutritional supplement comprising:
    about one half ounce of ground walnuts;
    three ground nubbins dark chocolate;
    ground no-calorie caramel;
    high fiber filler;
    up to about 2500 IU of vitamin A;
    about 2 mg of vitamin B6;
    about 400 mcg of vitamin B12;
    about 500 mg of vitamin C;
    up to about 1000 IU of vitamin D;
    about 500 IU of vitamin E;
    about 400 mcg of folate;
    about 12.5 mg of Thiamin;
    about 12.5 mg of Riboflavin;
    about 15 mg of Niacin;
    about 150 mg of Biotin;
    about 150 mg of Pantothenic acid;
    up to about 1600 mg of Calcium;
    up to about 400 mg of Magnesium;
    about 100 mcg of Selenium;
    about 7.5 mg of Zinc;
    about 30 mg of Lycopene;
    about 20 mg of Lutein;
    up to about 200 mg of Alpha lipoic acid;
    up to about 1500 mg of Acetyl-L-carnitine;
    up to about 400 mg of Coenzyme Q10;
    up to about 70 mg l-arginine;
    up to about 180 mg tyrosine;
    up to about 70 mg taurine;
    up to about 120 mg green tea catechin;
    up to about 20 mg caffeine; and
    up to about 10 mg quercetin.

8. The nutritional supplement product for inhibiting the progression of cognitive impairment in a non-statin user according to claim 7, further comprising a preserving substance comprising a substantially non-reactive fluid.

9. The nutritional supplement product for inhibiting the progression of cognitive impairment in a non-statin user according to claim 8, wherein the substantially non-reactive fluid comprises nitrogen gas.

10. The nutritional supplement product for inhibiting the progression of cognitive impairment in a non-statin user according to claim 8 where the nutritional supplement product is of the form taken from the group consisting of a bar, a smoothie, a frozen desert, and a beverage.

* * * * *